United States Patent [19]

Linnenbach et al.

[11] Patent Number: 5,668,002
[45] Date of Patent: Sep. 16, 1997

[54] DNA AND POLYPEPTIDE FOR TUMOR-ASSOCIATED ANTIGEN CO-029

[75] Inventors: Alban J. Linnenbach, Philadelphia; Hilary Koprowski, Wynnewood; Stanislaw Szala, Philadelphia, all of Pa.

[73] Assignee: The Wistar Institute, Philadelphia, Pa.

[21] Appl. No.: 575,567

[22] Filed: Aug. 31, 1990

[51] Int. Cl.$^6$ .......................... C10N 15/00; C07K 14/00; C07H 21/02; C07H 21/04

[52] U.S. Cl. .................. 435/325; 435/172.3; 435/354; 435/365; 435/366; 536/23.1; 536/23.5; 530/350

[58] Field of Search ...................... 435/240.2, 172.3; 530/395; 935/6, 10, 12, 13, 48

[56] References Cited

U.S. PATENT DOCUMENTS 4,870,008  9/1989  Brake et al. ............................. 435/70

FOREIGN PATENT DOCUMENTS 0 376746   7/1990  European Pat. Off. .
WO 89/04841  6/1989  WIPO .

OTHER PUBLICATIONS

Koprowski, et al., "Colorectal Carcinoma Antigens Detected by Hybridoma Antibodies", Somatic Cell Genetics, vol. 5, No. 6, 1979, pp. 957–972.

Hotta, et al., "Molecular Cloning and Characterization of an Antigen Associated with Early Stages of Melanoma Tumor Progression", Cancer Research, vol. 48, No. 11, pp. 2955–2962, Jun. 1, 1988.

Classon, et al., "The Primary Structure of the Human Leukocyte Antigen CD37, A Species Homologue of the Rat MRC OX–44 Antigen," The Journal of Experimental Medicine, vol. 169, No. 4, pp. 1497–1502, Apr. 1989.

Sela, et al., "Colon Carcinoma–Associated Glycoproteins Recognized by Monoclonal Antibodies CO–029 and GA22–2," Hybridoma, vol. 8, No. 4, 1989.

Wright et al., "An Immunogenic M 23,000 Integral Membrane Protein of Schistosoma mansoni Worms that Closely Resembles a Human Tumor–Associated Antigen," The Journal of Immunology, vol. 144, No. 8, pp. 3195–3200, 1990.

Szala, et al., "Molecular Cloning of cDNA for the Carcinoma–Associated Antigen GA733–2," Proc. Natl. Acad. Sci., vol. 87, pp. 3542–3546, May 1990.

Koprowski, Hilary et al., 5 Somatic Cell Genetic, No. 6, 957–971 (1979).

Steplewski, Zenon et al., XX Methods in Cancer Research 285–316 (1982).

Seed et al PNAS 84: 3365. 1987.

Szala et al PNAS 87: 6833. 1990.

Szala et al PNAS 87: 3542. 1990.

Sela et al Hybridoma 8 (4): 481. 1989.

*Primary Examiner*—Suzanne E. Ziska
*Attorney, Agent, or Firm*—Banner & Witcoff, Ltd.

[57] ABSTRACT

The human tumor-associated antigen CO-029 is a monoclonal antibody-defined, 27–34 kDa cell surface glycoprotein. A full-length cDNA clone for CO-029 is described. When transiently expressed in COS cells, the cDNA clone directs the synthesis of an antigen reactive with monoclonal antibody CO-029 in mixed hemadsorption and immunoblot assays. Sequence analysis reveals that CO-029 belongs to a family of cell surface antigens which includes the melanoma-associated antigen ME491, the leukocyte cell surface antigen CD37, and the Sm23 antigen of the parasitic helminth *Schistosoma mansoni*.

20 Claims, 9 Drawing Sheets

FIG. 1A
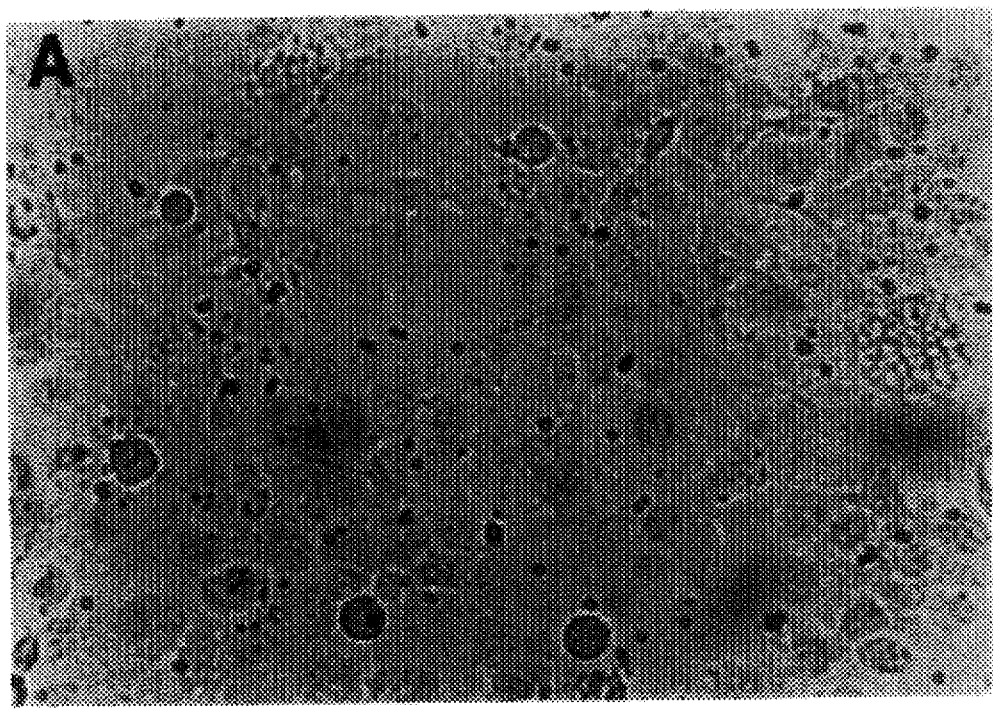
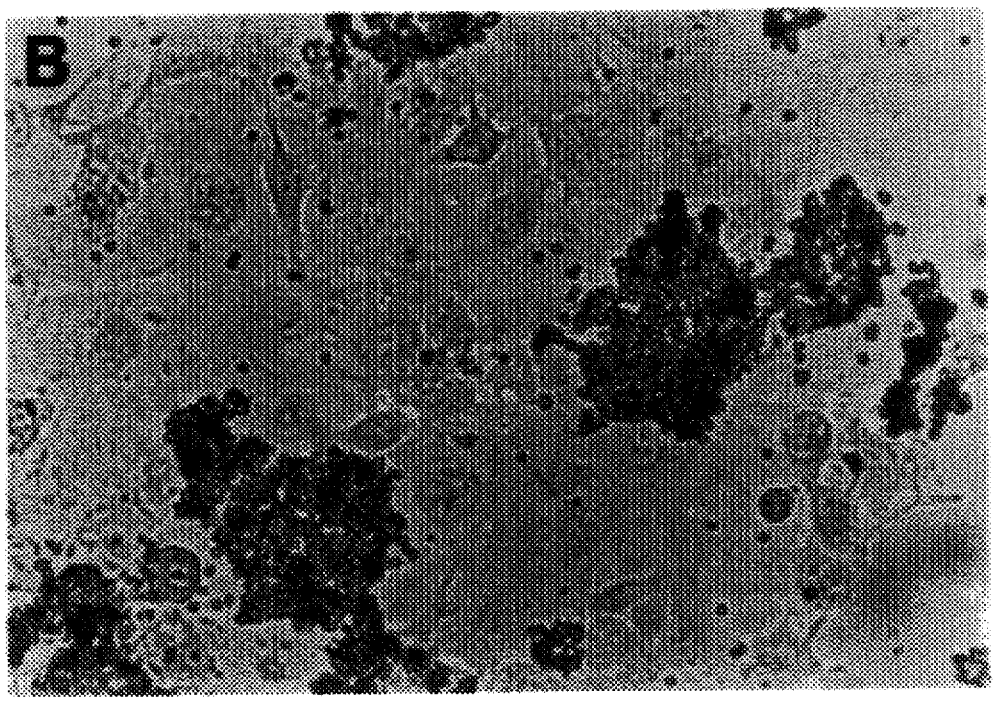
FIG. 1B

FIG. 3A(1)

```
  1  CTCTAGAGTCGAGATCCATTGTGCTCTAAAGTGATACAGAAATCTCTGCAGGCAAGT

1
                                              M  A  G  V  S  A  Ⓒ  I  K  Y  S  M  F  T
121  CCTAATCCTTTTCCGAAATGGCAGTGTGAGTGCCTGTATAAATATTCTATGTTTAC
                                                                              50
      S  N  D  S  Q  A  I  F  G  S  E  D  V  G  S  S  S  Y  V
241  TAAGCAATGACTCTCAAGCAATTTTGGTTCTGAAGATGTAGGCTCCTAGCTCCTACGT

G  A  I  K  E  S  R  Ⓒ  M  L  L  F  F  I  G  L  L  L
361  GCGGTGCTATAAAGAAAGTCGCTGCATGCTCCTGTTGTTTTCATAGGCTTGCTTCT

I  V  N  E  T  L  Y  E  N  T  K  L  L  S  A  T  G  E  S
481  GCATTGTGAATGAAACTCTATGAAAACACAAAGCTTTTGAGCGCCACAGGGAAAG

N  G  A  A  D  W  G  N  N  F  Q  H  Y  P  E  L  Ⓒ  A Ⓒ
601  TCAATGGAGCTGCTGATTGGGGAAATAATTTCAACACTACCTGAATTATGTGCCTG
                    200
      S  F  I  K  D  F  L  A  K  N  L  I  I  V  I  G  I  S  F
721  TTTCTTTCATAAAGACTTCTTGGCAAAAAATTTGATTATAGTTATTGGAATATCATT

N  K  *
841  GGAACAAATGAATCTGTGATGCATCAACCTATCGTCAGTCAAACCCCTTTAAAATGT
961  AAAATGTCTCGGCTAGCTAGACCACCAGATATCTCTTAGACATATTGAACACATTAAG
1081 TTT(A)₂₁   1104
```

FIG. 3A(2)

```
TGCTCCAGAGCATATTGCAGGACAGCCTGTAACGAATAGTTAAATTCACGGCATCTGGATT

F  N  F  L  F  W  L ⓒ G  I  L  I  L  A  L  A  I  W  R  V
CTTCAACTTCTGTTCTGGCTATGTGGCATCTTGATCCTAGCATTAGCAATATGGTACGAG

A  V  D  I  L  I  A  V  G  A  I  I  M  I  L  G  F  L  G ⓒⓒ
TGCTGTGGACATATTGATTGCTGTAGGTGCCATCATGATTCTGGGCTTCCTGGGATGCT
                                  100
  I  L  L  L  Q  V  A  T  G  I  L  G  A  V  F  K  S  K  S  D  R
GATCCTGCTCCTGCAGGTGGCGACAGGTATCCTGGGAGCTGTGTTTCAAATCTAAGTCTGATC

E  K  Q  F  Q  E  A  I  I  V  F  Q  E  E  F  K ⓒ G  L  V
TGAAAAACAATTCCAGGAAGCCATAATTGTGTTTCAAGAGAGTTTAAATGCTGGGGTTTGG
                                              150
  L  D  K  Q  R  P ⓒ Q  S  Y  N  G  K  Q  V  Y  K  E  T ⓒ I
TCTAGATAAGCAGAGACCATGCCAAAGCTATAATGGAAAACAAGTTTACAAAGAGACCTGTA

G  L  A  V  I  E  I  L  G  L  V  F  S  M  V  L  Y ⓒ Q  I  G
TGGACTGGCAGTTATTGAGATACTGGGTTTGGTGTTTCTATGCCTCCTGTATTGCCAGATCG

TGCTTTGGCTTTGTAA͞A͞T͞T͞AAATATGTAAGGAAAATATGTCTATATAAGTCAGGAGCAGCTGTCTTTT
ATTTGAGGGATATAAGCGAAAATGATATAAGTGTATTTTACTCAAAATAAAAGTAACTG
```

```
                                                                                          FIG. 4B
                                                                                    Ex I
Cons.    ..a.eggm.c  iKy.lfv.nl  .fllcg.l.i  a.giwv.v..  s...i......
                        Cy I                    Tm I
CO-029   ...MAGVSAC  IKYSMFTFNF  LFWLCGILIL  ALAIWVRVSN  DSQAIFGSED
ME491    ...MAVEGGMKC VKFLLYVLLL AFCACAVGLI  AVGVGAQLVL  SQTII...Q
Sm23     .MATLGTGMRC LKSCVFVLNI  ICLLCSLVLI  GAGAYVEVKF  SQYG....DN
CD37     MSAQESCLSL  IKYFLFVFNL  FFLVLGSLIF  CFGIWILIDK  TSFVSFVGLA 101                                                          Ex II
Cons.    ..vaa.Ilg.  vf.dk.d.e.  n.........  ..a......k.  ..e....Q.
CO-029   LQVATGILGA  VFKSKSDRIV  NETLYENTKL  LSATGESEKQ  FQEAIIVFQE
ME491    VEVAAAIAGY  VFRDKVMSEF  NNNFRQQMEN  YPKNNHTASI  LDR....MQA
Sm23     AELAAAIVAV  VYKDRIDSEI  DALM......  TGALDKPTKE  ITEFMNLIQS
CD37     TQITLGILIS  TQRAQLERSL  RD........  ..........  ..........

201                                                   247
Cons.    vs.ig.fL.k  Nl.iVa...af G.af.e.Lgi Vfaccl..qI .........VM
                                   Tm IV                   Cy III
CO-029   ISFIKDFLAK  NLIIVIGISF  GLAVIEILGL  VFSMVLYCQI  GNK......
ME491    VEKIGGWLRK  NVLVVAAAAL  GIAFVEVLGI  VFACCLVKSI  RSGYEVM
Sm23     VSVFGAFLKR  NLVIVACVAF  GVCFFQLLSI  VIACLGRQI   KEYENV.
CD37     ..........  ..........  ..........  ..........  .......
```

```
                                                                              100
         ....ap.  v.iavGv.im ivafIGCCGA iKEnrC.l.l  ..ifLll.ll
                            Tm II                   Cy II       Tm III
         VGSSSYVAVD ILIAVGAIIM ILGFLGCCGA IKESRCMLLL FFIGLLLILL
         GATPGSLLPV VIIAVGVFLF LVAFVGCCGA CKENYCLMIT FAIFLSLIML
         LHKVWQAAPI AIIVVGVIIL IVSFLGCCGA IKENVCMLYM YAFFLVVLLI
         FVPLQ.IWSK VLAISGIFTM GIALLGCVGA LKELRCLLGL YFGMLLLLFA 200
         .FkCCGa.n. ..d....... ........ ....p..c.. ....p..... nek..ykEg
         EFKCCGLVNG AA...DWGNN FQHYPELCAC LDKQRPCQSY NGKQVYKETC
         DFKCCGAANY TDWEKIPSMS KNRVPDSCCI NVIVGCGINF NEKAIHKEGC
         SFHCCGAKGP DDYRGNV... .......... ..........PASCK EENLYTYEGC
         ..........
```

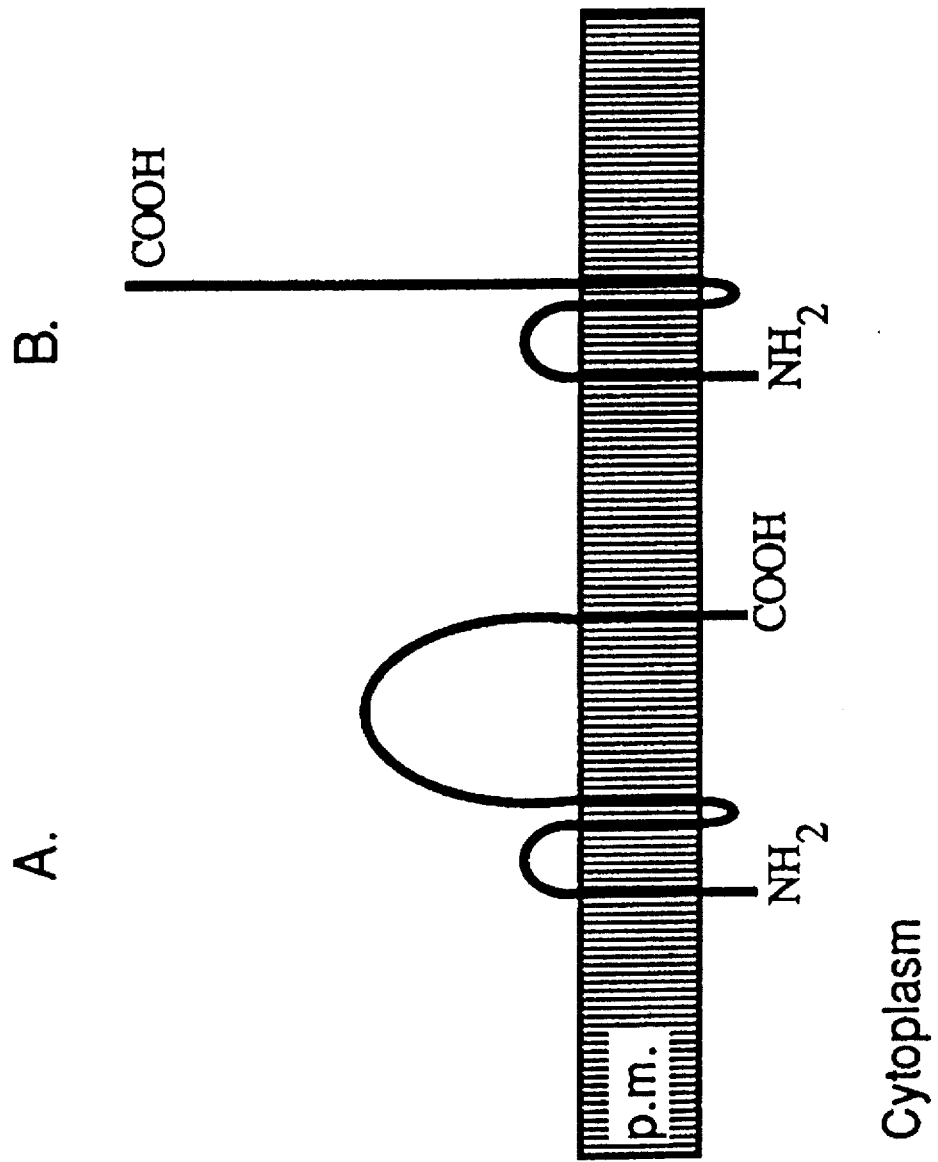

1.15 kb —

α-enolase —

DNA AND POLYPEPTIDE FOR TUMOR-ASSOCIATED ANTIGEN CO-029

The U.S. Government retains some rights in this invention which was made under grant CA21124-11 from the National Institutes of Health.

BACKGROUND OF THE INVENTION

A number of monoclonal antibodies (mAb) have been derived from the immunization of mice with human gastrointestinal tumor cell lines (Koprowski, et al., (1979), Somat. Cell Genet. vol. 5, pp. 957–972; Steplewski, et al., (1982) in Methods in Cancer Research, eds. Busch, et al., (Academic, New York), vol. XX. pp. 285–316; Herlyn, et al., (1984), J. Immunol. Meth., vol. 73, pp. 157–167; Gottlinger, et al., (1986), Int. J. Cancer, vol. 38, pp. 47–53; Girardet, et al., (1986), J. Immunol., vol. 136, pp. 1497–1503). Investigations into the antigenic structures recognized by these mAb have identified a group of glycolipid and glycoprotein antigens (Steplewski, et al., (1982) in Methods in Cancer Research, eds. Busch, et al., (Academic, New York), vol. XX, pp. 285–316). The 40 kDa cell surface glycoprotein (Ross, et al., (1986), Hybridoma, vol. 5, pp. S21–S27) recognized by mAb CO17-1A (Herlyn, et al., (1986), Hybridoma, vol. 5, pp. S3–S8), and several other independently derived mAb (Gottlinger, et al., (1986), Int. J. Cancer, vol. 38, pp. 47–53; Girardet, et al., (1986), J. Immunol., vol. 136, pp. 1497–1503; Ross, et al., (1986), Biochem. Biophys. Res. Comm., vol. 135, pp. 297–303), is one of the most well-characterized tumor-associated antigens. Another cell surface glycoprotein antigen, defined by mAb CO-029 (formerly called 1116NS-29) (Koprowski, et al., (1979), Somat. Cell Genet. vol. 5, pp. 957–972), has been shown to be a ~32 kDa monomer (Sela, et al., (1989), Hybridoma, vol. 8, pp. 481–491). The CO-029 antigen was found to be expressed on gastric, colon, rectal, and pancreatic carcinomas, but not on most normal tissues (Sela, et al., (1989), Hybridoma, vol. 8, pp. 481–491). MAb CO-029 has been shown to mediate antibody-dependent cell-mediated cytotoxicity in vitro (Koprowski, et al., (1979), Somat. Cell Genet. vol. 5, pp. 957–972). However, the CO-029 antigen has not been structurally characterized, nor has its coding sequence been isolated.

The recent molecular cloning of cDNA for tumor-associated antigens has provided information about antigen structure and the evolution of the genes encoding these antigens. cDNA clones have been isolated (Szala, et al., (1990), Proc. Natl. Acad. Sci. U.S.A., vol. 87, pp. 3542–3546) for the GA733-2 carcinoma-associated antigen defined by mAB GA733 (Herlyn, et al., (1986), Hybridoma, vol. 5, pp. S21–S27). Transfection experiments with a GA733-2 cDNA clone have shown that it encodes both the GA733 and CO17-1A epitopes (Szala, et al., (1990), Proc. Natl. Acad. Sci. U.S.A., vol. 87, pp. 3542–3546). Sequence analysis of GA733-2 found it to be identical with the mAb defined, tumor-associated antigen KSA (Strand, et al., (1989), Cancer Res., vol. 49, pp. 314–317). A related gene, GA733-1, has been identified and was found to have a 50% amino acid sequence homology with the GA733-2 antigen (Szala, et al., (1990), Proc. Natl. Acad. Sci. U.S.A., vol. 87, pp. 3542–3546; Linnenbach, et al., (1989), Proc. Natl. Acad. Sci. U.S.A., vol. 86, pp. 27–31). GA733-1 is an intronless gene that was shown to be transcribed at high levels in pancreatic carcinoma cell lines (Linnenbach, et al., (1989), Proc. Natl. Acad. Sci. U.S.A., vol. 86, pp. 27–31). The GA733 family of antigens are type I transmembrane proteins of unknown function.

There is a need in the art for additional cloned tumor-associated antigens. The clones can be used to determine nucleic acid sequences as well as to produce preparations of antigens which may be useful as vaccines to stimulate anti-tumor antibody production in cancer patients.

SUMMARY OF THE INVENTION

It is an object of the invention to provide DNA molecules encoding tumor-associated antigen CO-029.

It is another object of the invention to provide DNA molecules which can be used to express antigen CO-029 in cultured cells.

It is yet another object of the invention to provide sequence analysis of the CO-029 antigen to determine the antigenically important portions of the molecule.

It is an object of the invention to provide polypeptides which consist essentially of the extracellular domains of tumor-associated antigen CO-029.

It is another object of the invention to provide polypeptides which are immunoreactive with CO-029.

These and other objects of the invention are provided by one or more of the embodiments described below. In one embodiment an intron-free DNA molecule is provided which encodes a tumor associated antigen, said antigen immunoreactive with monoclonal antibody CO-029.

In another embodiment a polypeptide is provided consisting essentially of an extracellular domain of CO-029.

In still another embodiment a preparation of CO-029 antigen is provided which is free of other human proteins.

In yet another embodiment of the invention transformed cells are provided which contain DNA molecules encoding CO-029 antigen.

These and other embodiments of the invention which will be described in more detail below, provide the art with an additional molecularly, cloned tumor-associated antigen. This allows the unlimited production of the antigen in cells which are not malignant and the potential use of the antigen as a biological response modifier to stimulate the immune systems of human cancer patients to combat colorectal, lung and other carcinomas as well as astrocytomas.

BRIEF DESCRIPTION OF THE DRAWINGS

FIG. 1 shows the detection of the CO-029 antigen in transfected COS by mixed hemadsorption assay (MHA). Cells were incubated with mAb CO-029, and then reacted with an indicator system consisting of sheep erythrocytes treated with mouse antiserum against sheet erythrocytes and goat anti-mouse IgG. (A) Untreated COS cells. (B) COS cells 3 days after transfection with CO-029-5 DNA.

FIG. 4 shows alignment of CO-029 related sequences. The CO-029, ME491, and Sm23 sequences are shown in their entirety; the homologous portion of the CD37 sequence is presented. The single-letter amino acid code is used. Conserved Cysteine residues are in boldface type. Potential N-linked glycosylation sites (underline); and predicted transmembrane (Tm), extracellular (Ex) and cytoplasmic (Cy) domains are illustrated. Gaps (....) were inserted to maximize the alignment; a consensus sequence (Cons.) was calculated.

FIG. 5 shows models for the CO-029 family of membrane antigens. (A) The CO-029, ME491, and Sm23 antigens. (B) The CD37 antigen.

FIG. 7 shows the binding of monoclonal antibodies (mAbs) ME491 and CO-029 in radioimmunoassay (RIA) to a panel of human tumor cell lines. Results are presented after subtraction of non-specific mAb P3 binding (typically 100–200 cpm).

DETAILED DESCRIPTION

Figure 2:
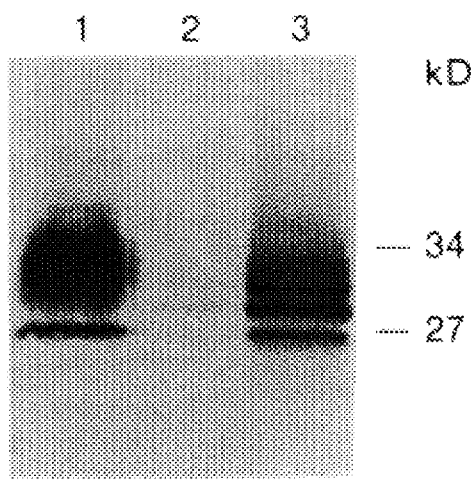
FIG. 2 shows Western blot detection of the CO-029 antigen in transfected COS cells. Total cell extracts were derived from control SW948 colorectal carcinoma cells (lane 1), untreated COS cells (lane 2), and COS cells 3 days after transfection with CO-029-5 DNA (lane 3).

An intron-free DNA molecule has been cloned and analyzed which encodes the tumor-associated antigen CO-029. When the DNA molecule is transfected into COS cells which do not express the antigen, the resulting transfectants synthesize antigen bearing the CO-029 epitope (as defined by the monoclonal antibody CO-029.) The antigen expressed in transfected COS cells is indistinguishable by Western blotting from that expressed in cells of a colorectal cell line.

DNA sequencing of the cloned DNA molecule reveals an antigen with a protein molecular weight of 26,044. This implies that up to 8 kDa of the native glycoprotein antigen may be due to glycosylation. The complete nucleic acid and predicted amino acid sequences are shown in FIG. 3.

DNA molecules and polypeptides according to the present invention may contain all or part of the sequences shown in FIG. 3. Desirably polypeptides retain the ability to bind to antibodies which are immunoreactive with the extracellular domains of CO-029. Such binding can be readily tested by raising antibodies against a particular polypeptide. If the antibodies immunoreact with intact colorectal carcinoma cells which express the antigen on their cell surfaces, the polypeptide represents an extracellular epitope. As taught herein, one such extracellular domain comprises amino acids numbered 34 to 57, and another comprises amino acids 110 to 205. In one embodiment of the invention the polypeptide is immunoreactive with monoclonal antibody CO-029. In another embodiment of the invention a polypeptide is covalently linked to an amino acid sequence which causes the polypeptide to be secreted from cells in which it is synthesized. Such amino acid sequences, signal sequences, are well known in the art.

Polypeptides of the present invention may be free of glycosylation. Such glycosylation-free polypeptides can be synthesized for example in a non-glycosylating microorganism such as E. coli, or in the presence of tunicamycin in cells which do glycosylate mammalian proteins. Alternatively the polypeptides can be chemically synthesized, for example using an automatic synthesizer, according to the disclosed sequence. Glycosylated polypeptides can be made in mammalian and other higher eukaryotic cells.

Because the polypeptides of the invention can be made by recombinant DNA-containing organisms or cells or synthetically, they can be entirely free of other human proteins. In contrast, native antigens isolated from human cells generally do not achieve such a level of purity. Since the polypeptide need not be isolated from malignant human cells, there is reduced risk associated with administration of the polypeptide to humans, for example, as an injectible.

The polypeptides of the present invention can be used to raise new anti-tumor antibodies. It may be desirable to isolate antibodies which are reactive with other epitopes of the CO-029 antigen than the one defined by monoclonal antibody CO-029. Alternatively, it may be desirable to isolate antibodies which react with the same epitope but have different properties from CO-029, such as enhanced or reduced cytotoxicity. The polypeptides can also be used as mentioned above, as injectibles. They can be used as biological response modifiers to stimulate a cancer patient's immune system to attack tumors expressing the CO-029 antigen.

The polypeptides of the invention may be coupled to larger moieties, such as keyhole limpet hemocyanin, to enhance their immunogenicity. They can also be mixed with adjuvants, as is known in the art. In one particular embodiment the polypeptide is mixed with vital proteins of vaccinia. This is conveniently achieved by forming recombinant vaccinia virus genomes which express the CO-029-related polypeptide. The recombinant virus can be grown in baby hamster kidney cells (BHK) for example, and the recombinant virus injected into humans. The polypeptides of the present invention can also be mixed with other bioactive or immunologically active polypeptides.

Polypeptides of the invention may also be used diagnostically to quantitate the amount of antigen present in a biological sample. For example, defined amounts of polypeptide can be used in competitive binding assays with antibodies directed against the polypeptide.

The DNA molecules of the present invention can be used to express the antigens of the invention. The DNA molecules are used to transform suitable human or non-human cells, such as mouse, monkey, yeast, etc. Methods of transforming and propagating such cells in culture are well known. In one embodiment the antigen-coding DNA molecule is linked to a vector which can replicate in E. coli. Such vectors are well-known in the art. In another embodiment the DNA molecule causes COS cells to express a protein which is immunoreactive with monoclonal antibody CO-029. Such expression may be stable or transient, depending on the vector used for transfection. Portions of the CO-029 gene can be isolated using the polymerase chain reaction (PCR). For example, the portion of the gene encoding the large extracellular domain can be amplified and isolated using primers designed from the disclosed sequence. This can be ligated to DNA encoding a signal sequence so that when expressed in a recombinant cell the extracellular domain is expressed and secreted from the cell. Suitable signal sequences are known in the art.

DNA molecules can also be used as probes and primers in polymerase chain reactions or hybridization studies to quantitate expression of the CO-029 mRNA in a biological sample. Such quantitation may provide diagnostic or prognostic information on a patient's disease. Thus the DNA molecules of the invention may be as small as about 10 nucleotides and be useful as probes or primers, if they hybridize specifically to the CO-029 gene. Some DNA molecules of the invention are only as large as is necessary to encode a polypeptide which is immunoreactive with antibodies raised using the entire CO-029 antigen as an immunogen.

The following examples illustrate further aspects of the invention but do not limit the invention to these particular embodiments.

EXAMPLES

Example 1

Immunoselection of cDNA Clones

A cDNA library (Szala, et al. (1990), Proc. Natl. Acad. Sci. U.S.A., vol. 87, pp. 3542–8546) prepared from the SW948 colorectal carcinoma cell line was transfected into COS cells by the DEAE-dextran method (Seed, et al. (1987), Proc. Natl. Acad. Sci. U.S.A., vol. 84, pp. 3365–3369). COS cells transiently expressing antigen were selected by "panning" (Seed, et al. (1987), Proc. Natl. Acad. Sci. U.S.A., vol. 84, pp. 3365–3369) with mAb CO-029. Episomal DNA was recovered from the panned cells and transferred into *Escherichia coli* MC1061/P3 cells. Recombinant DNA was isolated from the *E. coli* cells and further enriched for CO-029 sequences by two additional cycles of immunoselection, with COS cells (African Green Monkey Kidney Cells) transfections being performed by spheroplast fusion (Seed, et al. (1987), Proc. Natl. Acad. Sci. U.S.A., vol. 84, pp. 3365–3369) instead of DEAE-dextran. The first immunoselection of the total cDNA library yielded 11,600 drug resistant bacterial colonies; 600 and 2900 colonies were observed after the second and third selections, respectively.

Example 2

Analysis of Immunoselected Clones

Ten drug-resistant bacterial colonies resulting from the final selection were chosen at random and analyzed for cDNA insert size by digestion at flanking XhoI sites. Six out of 10 clones contained cDNA inserts 1.1 kb in size. DNA was prepared from a 1.5 ml bacterial culture of one of the clones, CO-029-5. One-fifth of this DNA was introduced into COS cells by the DEAE-dextran method. After a 3 day transient expression period, the transfectants were analyzed with mAb for the expression of the CO-029 epitope.

Transfected cells were assayed by the mixed hemadsorption assay (MHA) as described by Herlyn, et al. (Cancer Res., (1980), vol. 40, pp. 3602–3609). In MHA using mAb CO-029, ~30% of transfected COS cells rosetted (FIG. 1B), whereas untreated COS cells did not react (FIG. 1A).

To confirm this result, Western blot analysis with mAb was performed on COS cells transiently expressing the CO-029-5 clone. For Western blot analysis, cells were lysed in a buffer containing NP-40 (Ross, et al., (1986), Biochem. Biophys. Res. Comm., vol. 135, pp. 297–303), and 40 µg aliquots of non-reduced, non-heated, total protein were electrophoresed on a 12% SDS-polyacrylamide gel (Laemmli, (1970), Nature (London), vol. 227, pp. 680–685). Proteins were electroblotted onto a nitrocellulose filter, which was incubated with affinity purified CO-029 mAb at 1 µg/ml, and then with affinity purified goat anti-mouse IgG alkaline phosphatase conjugate and substrates for color development (Promega Biotech, Madison, Wis.).

Transfected cells expressed a 27–34 kDa antigen (FIG. 2, lane 3) characteristic of the native CO-029 antigen expressed in control SW948 cells (FIG. 2, lane 1). Both cell types expressed several discrete forms of CO-029 between 27 and 34 kDa. Antigen was not detected in untreated COS cells (FIG. 2, lane 2). Thus, the CO-029-5 clone encoded the epitope recognized by the CO-029 mAb.

Example 3

DNA Sequence Determination and Analysis

Both strands of the full-length cDNA clone CO-029-5 were sequenced by the dideoxynucleotide method (Sanger, et al. (1977), Proc. Natl. Acad. Sci. U.S.A., vol. 74, pp. 5463–5467). Sequence reactions were performed with T7 DNA polymerase (Pharmacia, Piscataway, N.J.) using vector-specific and CO-029-specific primers. Compressions were resolved by substituting 7-deaza dGTP for dGTP.

The 1.1 kb sequence of CO-029-5 revealed an open reading frame for 237 amino acids beginning at the 5'-proximal ATG codon, which was found to be flanked by sequences similar to the consensus sequence for initiation of translation (Kozak, (1987), Nucleic Acids Res., vol. 15, pp. 8125–8147) (FIG. 3A). A protein molecular weight of 26,044 is predicted for CO-029. Thus, up to 8 kDa of the 27–34 kDa CO-029 glycoprotein may be accounted for by glycosylation (Sela, et al. (1989), Hybridoma, vol. 8, pp. 481–491). A single potential N-linked glycosylation site was observed (FIG. 3A). The 5' untranslated region consists of 138 residues; the 232 base 3' untranslated region contained one consensus sequence for poly(A) addition and two sequences for mRNA turnover (Shaw, et al., (1986), Cell, vol. 46, pp. 659–667) (FIG. 3A).

Figure 3B:
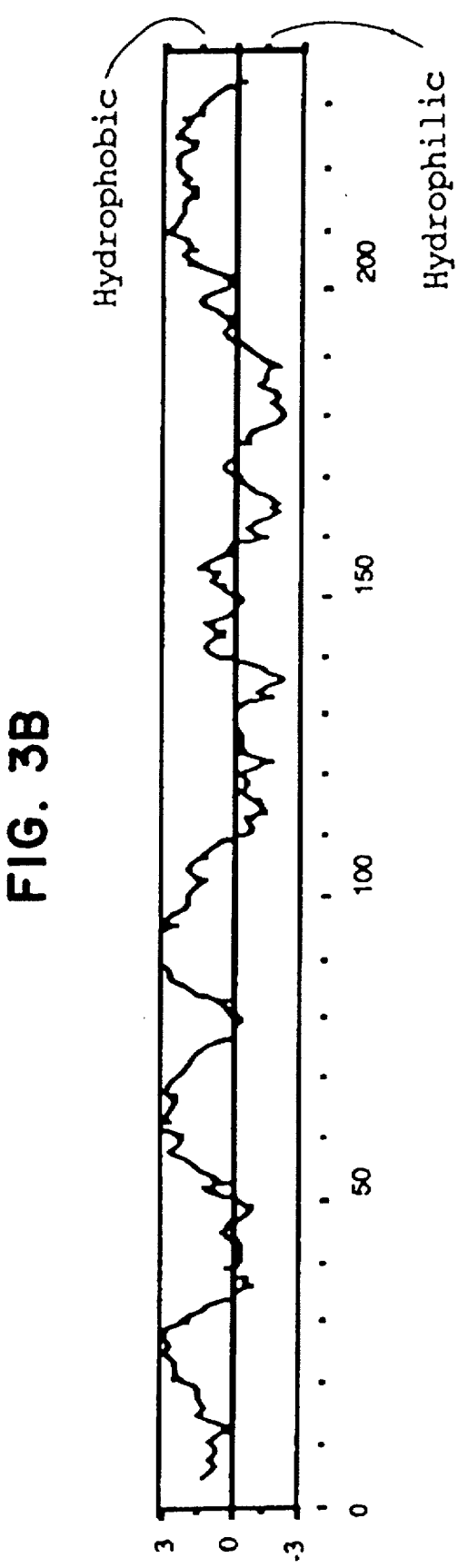
FIG. 3 shows (A) the sequence of full-length CO-029 cDNA with predicted amino acid sequence. The single-letter amino acid code is used. The positions of 12 Cysteine residues (circles), a potential N-linked glycosylation site (dotted overline), and 4 hydrophobic regions (bold overline) are indicated. Consensus sequences for initiation of translation (underline), mRNA turnover (overline) and poly(A) addition (dotted underline) are shown. (Panel B) shows a Kyte-Doolittle hydrophobicity plot of the CO-029 antigen showing the 4 hydrophobic regions.

Analysis of the distribution of hydrophobic and hydrophilic amino acids (Kyte, et al., (1982), J. Mol. Biol., vol. 157, pp. 105–132) (FIG. 3B) suggested that CO-029 is a type III integral transmembrane protein (Singer, et al., (1987), Proc. Natl. Acad. Sci. U.S.A., vol. 84, pp. 1960–1964) Four hydrophobic stretches of ~25 amino acids were found to be separated by hydrophilic amino acids (FIGS. 3A and B).

The CO-029 sequence was tested for homology by searching release 63 of GenBank with the program TFASTA (Pearson, et al. (1988), Proc. Natl. Acad. Sci. U.S.A., vol. 85, pp. 2444–2448), and release 23 of the NBRF-protein database with the programs FASTP (Lipman, et al. (1985), Science, vol. 227, pp. 1435–1441) and FASTA (Pearson, et al. (1988), Proc. Natl. Acad. Sci. U.S.A., vol. 85, pp. 2444–2448). Sequences with optimized scores >100 were further studied with the programs ALIGN (Dayhoff, et al., (1983) in Methods in Enzym., eds. Hirs, et al., (Academic, New York), vol. 91, pp. 524–545) and LINE-UP (Devereux, et al., (1984), Nucleic Acids Res., vol. 12, pp. 387–395).

Database analysis revealed that the CO-029 antigen was related to the human melanoma-associated antigen ME491 (Hotta, et al., (1988), Cancer Res., vol. 48, pp. 2955–2962) and the human leukocyte antigen CD37 (Classon, et al., (1989), J. Exp. Med., vol. 169, pp. 1497–1502). Other investigators have found ME491 to be homologous to the Sm23 antigen of the parasitic helminth *S. mansoni* (Wright, et al. (1990), J. Immunol., vol. 144, pp. 3195–3200). Analysis of these sequences with the program ALIGN indicated that these homologies were statistically significant. For example, pairwise comparison of the CO-029 sequence with the ME491, Sm23, and CD37 sequences, using a gap penalty of 40, resulted in alignment scores 34, 30, and 18 SD units above the mean score of 100 random runs, respectively.

A multiple sequence alignment indicated that the positions of Cys and Gly residues were particularly well conserved in the CO-029 family (FIG. 4). Sequence homology was greatest in transmembrane and cytoplasmic domains predicted by hydrophobicity analysis (Kyte, et al., (1982), J. Mol. Biol., vol. 157, pp. 105–132) (data not shown). This homology was evident even in species as evolutionarily divergent as *Homo sapfens* and *S. mansoni*. For example, there were 10 consecutive amino acid identities occurring in CO-029 and Sm23 beginning at residue 74 of the alignment (FIG. 4). In contrast to the transmembrane and cytoplasmic domains, the extracellular domains probably have sustained insertions and/or deletions. The sequences of the predicted extracellular domains were divergent, with the exception of the positions of Cys residues. The number and positions of potential N-linked glycosylation sites varied amongst these antigens, but all positions corresponded to the major hydrophilic domains (FIG. 4).

Two classes of antigen could be distinguished within this family. CO-029, ME491, and Sm23 proteins were found to be approximately equal in length and homologous throughout (FIG. 4). In contrast, the homology of CD37 to CO-029, ME492, and Sm23 was limited to the $NH_2$-terminal half of these antigens (FIG. 4).

Assuming that the CO-029, ME491, and Sm23 proteins have four transmembrane domains and assuming that the positions of the potential N-linked glycosylation sites (FIG. 4) place the major hydrophilic domains outside the cell, these antigens would be orientated so that the $NH_2$ and COOH-terminal ends would be on the cytoplasmic side of the membrane (FIG. 5A). Two extracellular domains, and three short cytoplasmic domains were predicted (FIGS. 4 and 5A). The portion of CD37 homologous to the other CO-029-related antigens consisted of three transmembrane and two cytoplasmic domains (FIGS. 4 and 5B).

Example 4

CO-029 Expression in Tumor Cell Lines

Transcription of the CO-029 gene in human tumor cell lines was analyzed by RNA blotting. Two μg of poly A+ cytoplasmic mRNAs (Berger, et al., (1979), Biochemistry, vol. 18, pp. 5143–5149) were electrophoresed on a 2.2M formaldehyde/1% agarose gel (Lehrach, et al., (1977), Biochemistry, vol. 16, pp. 4743–4751) and transferred to nitrocellulose. The CO-029-5 cDNA clone was nick-translated and hybridized to the filter in a solution containing 50% deionized formamide and 5×SSC [20×SSC is 3.0M sodium chloride/0.3M sodium citrate, pH 7.0] at 42° C. overnight. The filter was washed at high stringency in 0.1×SSC/0.1% SDS at 65° C. The probe was then removed and the filter was hybridized to the control α-enolase cDNA probe (Giallongo, et al., (1986), Proc. Natl. Acad. Sci. U.S.A., vol. 83, pp. 6741–6745).

Figure 6A:
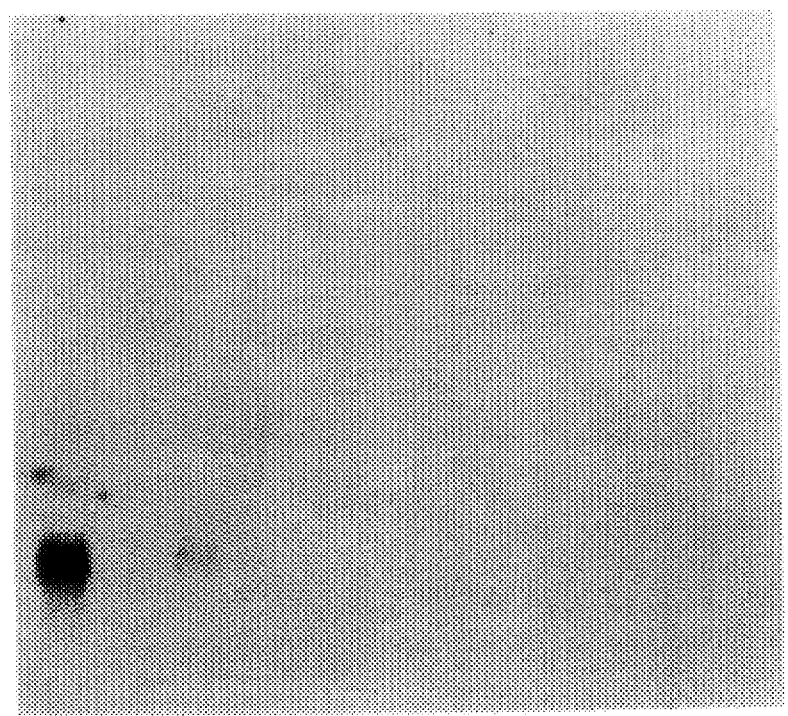
FIG. 6 shows in panel A a Northern blot analysis with the CO-029-5 DNA probe. mRNA was derived from the SW948 colorectal carcinoma cell line (lane 1), the SW707 rectal carcinoma cell line (lane 2), the pancreatic carcinoma cell lines Capan-2 (lane 3) and BXPC-3 (lane 4), the melanoma cell lines WM1158 (lane 5) and WM35 (lane 6). In panel B hybridization was performed with a control probe from the enolase gene.
Figure 6B:
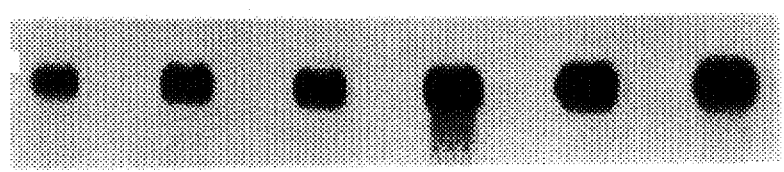

Transcription of the CO-029 gene was detected in the SW948 colorectal carcinoma and in the SW707 rectal carcinoma and cell lines (FIG. 6A, lanes 1 and 2). The steady state level of CO-029 mRNA differed in these two lines, while the level of α-enolase mRNA was approximately equal (FIG. 6B, lanes 1 and 2). The size of the full-length cDNA clone (FIG. 3A) correlated with the observed 1.15 kb CO-029 transcript. Two pancreatic carcinoma and two melanoma cell lines were negative for CO-029 mRNA (FIG. 6A, lanes 3–6). CO-029-related transcripts were not observed under the high stringency hybridization and washing conditions used here.

Example 5

Antigen Expression in Tumor Cell Lines

[$^3$H] thymidine incorporation was measured after incubation of cells with purified mAbs in chemically defined, serum-free medium. The colorectal carcinoma cell line SW948 and the melanoma cell line WM852 were aliquoted (100 μ) to 96-well plates at $1.5 \times 10^4$ cells/well. Aliquots of mAbs CO-029 and ME491 (100 μl and 5–250 μg/ml) were added to each cell type 18 hr after seeding. After 24 hr, each culture was pulsed for 18 hr with 1 μCi of [methyl $^3$H] thymidine (48 Ci/mmole; 1 Ci=37 GBq). Cells were trypsinized, collected with an automatic cell harvester (Skatron, Sterling, Va.), and cell-associated radioactivity was determined in triplicate by liquid scintillation counting.

CO-029 and ME491 antigen expression was compared in different tumor cell lies by RIA. Several cell lies co-expressed these genes (FIG. 7). The major qualitative difference in the expression of the two genes was that melanoma cell lines expressed the ME491 antigen but not the CO-029 antigen.

We claim:

1. An intron-free DNA molecule which encodes a tumor-associated antigen, said antigen immunoreactive with monoclonal antibody CO-029.
2. The intron-free DNA molecule of claim 1 wherein the tumor associated antigen has a protein molecular weight of 26,044.
3. The intron-free DNA molecule of claim 1 wherein the amino acid sequence of said antigen is shown in FIG. 3.
4. The intron-free DNA molecule of claim 1 wherein the nucleic acid sequence is shown in FIG. 3.
5. The intron-free DNA molecule of claim i which is covalently linked to a vector which can replicate in *E. coli*.
6. The intron-free DNA molecule of claim 1 which causes expression of a protein in COS cells immunoreactive with monoclonal antibody CO-029.
7. An intron-free DNA molecule comprising a nucleic acid sequence shown in FIG. 3.
8. An intron-free DNA molecule which hybridizes under stringent conditions to DNA having the sequence shown in FIG. 3.
9. An intron-free DNA molecule which codes for a polypeptide consisting essentially of an extracellular domain of the CO-029 antigen.
10. A polypeptide consisting essentially of an extracellular domain of the CO-029 antigen.
11. The polypeptide of claim 10 wherein the domain comprises amino acids 34 to 57 of CO-029.
12. The polypeptide of claim 10 wherein the domain comprises amino acids 110 to 205 of CO-029.
13. The polypeptide of claim 10 which is covalently linked to an amino acid sequence which causes said polypeptide to be secreted from cells.
14. A preparation of CO-029 antigen which is entirely free of other human proteins.
15. The preparation of claim 14 wherein the antigen is made in non-human cells which have been transformed with a DNA molecule encoding said antigen.
16. Non-human cells transformed with a DNA molecule encoding CO-029 antigen.
17. Cells transformed with the DNA molecule of claim 1.
18. Cells transformed with the DNA molecule of claim 7.
19. Cells transformed with the DNA molecule of claim 8.
20. Cells transformed with the DNA molecule of claim 9.

* * * * *